United States Patent [19]
Bennett et al.

[11] Patent Number: 6,031,154
[45] Date of Patent: Feb. 29, 2000

[54] FRUCTOKINASE GENES AND THEIR USE IN METABOLIC ENGINEERING OF FRUIT SWEETNESS

[75] Inventors: Alan B. Bennett, Davis, Calif.; Yoshinori Kanayama, Sendai, Japan

[73] Assignee: The Regents of the University of California, Oakland, Calif.

[21] Appl. No.: 08/826,611

[22] Filed: Apr. 5, 1997

[51] Int. Cl.$^7$ ............... C12N 15/29; C12N 15/54; C12N 15/82; C12P 19/04; A01H 5/00
[52] U.S. Cl. ............... 800/284; 800/263; 800/286; 800/287; 800/298; 800/317.4; 435/101; 435/194; 435/468; 536/23.6; 536/24.1; 536/24.5
[58] Field of Search ............... 800/263, 284, 800/286, 287, 298, 317.4; 435/69.1, 101, 194, 468; 536/23.6, 24.1, 24.5

[56] References Cited

U.S. PATENT DOCUMENTS

| | | | |
|---|---|---|---|
| 5,034,323 | 7/1991 | Jorgensen | 435/172.3 |
| 5,498,831 | 3/1996 | Burgess | 800/205 |

OTHER PUBLICATIONS

Deikman, J. et al. Organization of ripening and ethylene regulatory regions in a fruit–specific promoter from tomato (*Lycopersicon esculentum*). Plant Physiology 100:2013–2017 (1992).

Fillatti, J.J. et al. Efficient transfer of a glyphosate tolerance gene into tomato using a binary *Agrobacterium tumefaciens* vector. Biotechnology, 5:726–730 (1987).

Smith, S.B. et al. Primary structure and characterization of a cDNA clone of fructokinase from potato (*Solanum tuberosum* L.cv record). Plant Physiology 102:1043 (1993).

Martinez–Barajas, E., et al. (1996) "Purification and characterization of fructokinase from developing tomato (*Lycopersicon esculentum* Mill.) fruits", *Planta*, 199:451–458.

Doehlert, Douglas C. (1990) "Fructokinase from Developing Maize Kernels Differ in Their Specificity for Nucleoside Triphosphates", *Plant Physiol.* 93:353–355.

Copeland, Les, et al. (1978) "Fructokinase (Fraction III) of Pea Seeds", *Plant Physiol*, 62:291–294.

Chaubron, Franck, et al. (1995) "Partial purification and characterization of fructokinase from developing taproots of sugar beet (*Beta vulgaris*)", *Plant Science* 110:181–186.

Baysdorfer, Chris, et al. (1989) "Partial Purification and Characterization of Fructokinase Activity from Barley Leaves", *J. Plant Physiol.*, 134:156–161.

Gardner, Andrew, et al. (1992) "Purification and Properties of Fructokinase from Developing Tubers of Potato (*Solanum tuberosum* L. )", *Plant Physiol.*, 100:178–183.

Smith, Susan B., et al. (1993) "Primary Structure and Characterization of a cDNA Clone of Fructokinase from Potato (*Solanum tuberosum* L. cv Record)", *Plant Physiol.*, 102:1043.

(List continued on next page.)

*Primary Examiner*—David T. Fox
*Attorney, Agent, or Firm*—Townsend and Townsend and Crew LLP

[57] ABSTRACT

This invention provides for novel cDNA and regulatory DNA sequences which modify carbohydrate metabolism in ripening fruit. In order to suppress fructokinase gene expression in transgenic plants and their fruit, we have isolated the cDNA of two tomato fructokinase genes that are expressed in developing and ripening fruit. These cDNA sequences, antisense sequences or ribozymes can be used to suppress expression of the transgenic plant's endogenous genes in ripening fruit by the use of chimeric constructions of the cDNA or antisense using either constitutive or fruit-specific and ripening-regulating regulatory sequences.

In addition to a novel method of modifying carbohydrate metabolism, we have also found a novel fructokinase gene. Of the two tomato fructokinase genes described in this invention, one is highly homologous to previously described potato fructokinase gene; the other is highly divergent and represents a kinetically unique plant fructokinase.

28 Claims, 1 Drawing Sheet

OTHER PUBLICATIONS

Renz, Andreas, et al. (1993) "Substrate specificity and product inhibition of different forms of fructokinases and hexokinases in developing potato tubers", *Planta*, 190:166–175.

Taylor, Mark A., et al. (1995) "Characterisation of a cDNA Encoding Fructokinase from Potato (*Solanum tuberosum* L.)", *J. Plant Physiol.* 145:253–256.

Fennington, George J., et al. (1996) "The fructokinase from *Rhizobium leguminosarum* biovar trifolii belongs to group I fructokinase enzymes and is encoded separately from other carbohydrate metabolism enzymes", *Microbiology*, 142:321–330.

Kossman et al. Progress Biotechnol. 10:271–278, 1995.

von Schaewen et al. Embo J. 9(10):3033–3044, 1990.

Kanayama et al. Plant Physiol. 113(4)–1379–1384, 1997.

Martinez–Barajas et al. Plant Science 125(1):13–20, 1997.

FRUCTOKINASE GENES AND THEIR USE IN METABOLIC ENGINEERING OF FRUIT SWEETNESS

FEDERAL SPONSORSHIP OF RESEARCH OR DEVELOPMENT

This invention was made with Government support under Grant No. US-2451-94, awarded by the U.S.-Israel Binational Agricultural Research and Development. The Government has certain rights in this invention.

CROSS REFERENCE TO RELATED APPLICATIONS

Not Applicable

FIELD OF THE INVENTION

This invention relates to providing a genetic means to engineer metabolism of plants in such a way to elevate the levels of fructose in developing and ripening fruit.

BACKGROUND OF THE INVENTION

The single most important consumer-defined quality characteristic of fruit is flavor and in most fruit, consumer flavor preferences are dominated by sweetness. There is a well-characterized difference in sweetness of hexose sugars, with fructose being approximately twice as sweet as its hexose isomer, glucose.

The proportion of fructose in fruit is controlled, at least in part, by its conversion to fructose-6-phosphate by the hexose kinase, fructokinase. The hexose kinases can be divided into three general categories according to their hexose substrate specificity. Hexokinase (HK) can phosphorylate glucose and fructose, while glucokinase (GK) and fructokinase (FK) are relatively specific for the respective hexose isomer. Plant tissues may contain multiple hexose kinases and multiple isozymes of the enzymes.

Figure 1:
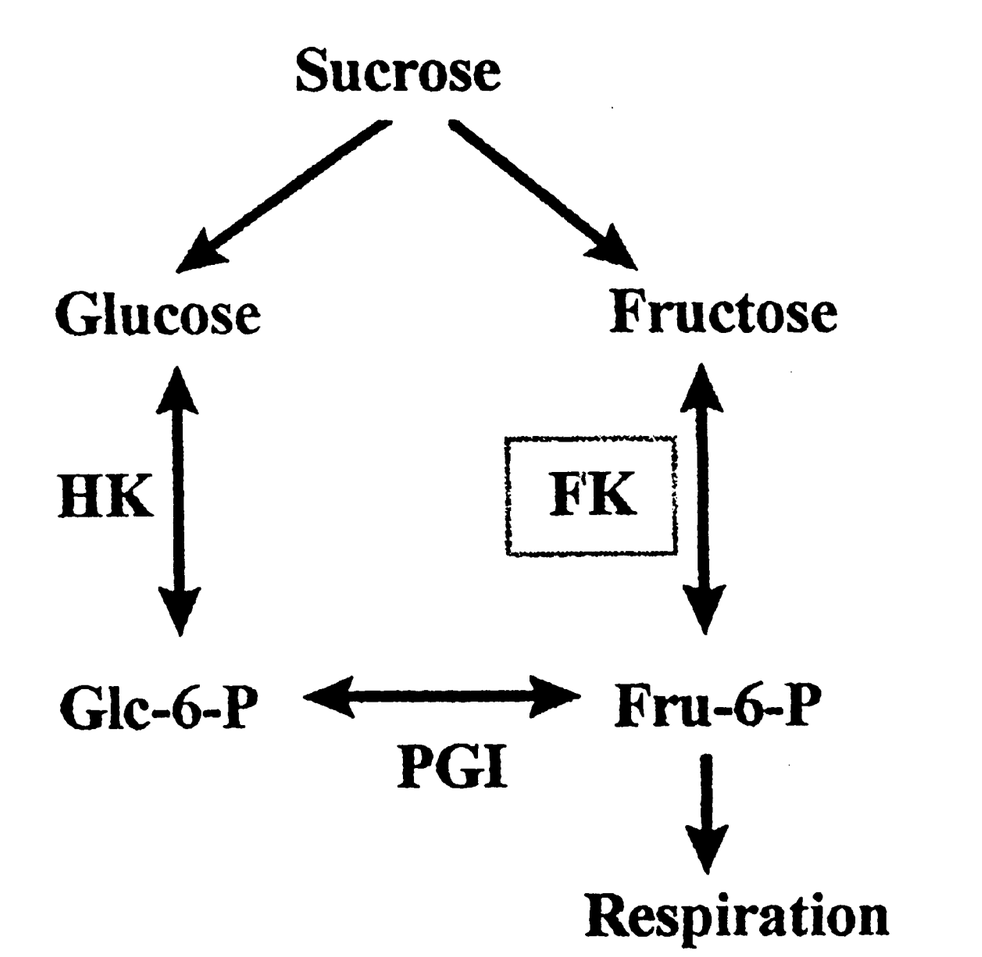
FIG. 1 illustrates the metabolism of imported sucrose into the flesh of fruit. HK=Hexokinase, FK=Fructokinase, Glc-6-P=Glucose-6-phosphate, Fru-6-P=Fructose-6-phosphate, PGI=phosphoglucose isomerase.

Carbohydrate metabolism and carbohydrate composition has previously been modified in transgenic plants by increasing starch levels or by altering the relative levels of sucrose in fruit. Several studies with fruit tissues have indicated that during the development and ripening of hexose-accumulating fruit, imported sucrose can be hydrolyzed by a hexose invertase into its two hexose moieties; fructose and glucose. The possible fates of the fructose and glucose moieties of imported sucrose after invertase-mediated hydrolysis are illustrated in FIG. 1. According to this model, the balance of the activities of hexokinase (HK), fructokinase (FK) and the hexose phosphatases (These enzymes dephosphorylate hexose-6-phosphates into hexoses) control levels of glucose-6-phosphate (Glc-6-P) and fructose-6-phosphate (Fru-6-P). Glc-6-P in turn isomerizes via phosphoglucose isomerase (PGI) to Fru-6-P, a reversible reaction that is predicted to be approximately at equilibrium in vivo. Fru-6-P then enters respiratory pathways. It is postulated these reactions serve to equilibrate Fru-6-P and Glc-6-P pools in fruit tissues, and as a consequence, also equilibrate glucose and fructose pools.

A fructokinase gene has been previously cloned from potato and the sequence of its cDNA determined (Smith, S. B., et al., *Plant Physiol.* 102:1043 (1993); Taylor, M. A., et al., *J. Plant Physiol.* 145:253 (1995)). In addition, fructokinase isozymes have been isolated and at least partially purified from barley leaves (Baysdorfer, C., et al., *J. Plant Physiol.* 134:156 (1989)); taproots of sugar beets (Chaubron, F., et al., *Plant Science* 110:181 (1995)); pea seeds (Copeland, 1., et al., *Plant Physiol.* 62:291 (1978)); maize kernels (Doehlert, D. C., *Plant Physiol.* 90:353 (1990)); and tomatoes (Martinez-Barajas, E., and Randall, D. D., *Planta* 199:451 (1996)).

Previous research has used traditional breeding practices to select for fruit varieties with enhanced sweetness. This has been achieved in many different varieties, e.g., supersweet corn and melons. In all cases, the increase in sweetness has been achieved by selecting for varieties with a higher concentration of total soluble sugars. However, in other fruit, such as the tomato, increases in the concentration of total soluble sugars is associated with a decline in total yield. Modern varieties, which have been selected to be high yielding, tend to have lower total sugar levels and reduced sweetness, relative to older cultivars. Thus, the prior art fails to provide a cost-effective means of producing plants with increased fructose levels but without undesired traits. The present invention addresses these and other needs.

SUMMARY OF THE INVENTION

The present invention is based, in part, on the isolation and characterization of a Frk1 gene. The invention provides isolated nucleic acid molecules comprising a Frk1 polynucleotide sequence, typically about 1900 nucleotides in length, which specifically hybridizes to SEQ ID NO: 1 under stringent conditions. The Frk1 polynucleotides of the invention can encode a Frk1 polypeptide of about 350 amino acids, typically as shown in SEQ ID NO: 2.

The nucleic acids of the invention may also comprise expression cassettes containing a plant promoter operably linked to the Frk1 polynucleotide. In some embodiments, the promoter is from a tomato E8 gene. The Frk1 polynucleotide may be linked to the promoter in a sense or antisense orientation.

The nucleic acids of the invention may also comprise two expression cassettes; the first comprising the Frk1 polynucleotide and the second comprising a Frk2 polynucleotide. The Frk2 polynucleotide may be operably linked to a promoter from the tomato E8 gene as well. The Frk2 polynucleotide may be linked to the promoter in a sense or antisense orientation.

The invention also provides transgenic plants comprising one or two expression cassettes containing a plant promoter operably linked to an Frk1 polynucleotide or an Frk2 polynucleotide. The Frk1 and or Frk2 may encode a Frk1 and or Frk2 polypeptide or may be linked to the promoter in an antisense orientation. The plant promoter may be from any number of sources, including the tomato E8 gene. The transgenic plant can be any desired plant but is often a member of the genus Lycopersicon.

Methods of inhibiting fructokinase expression in a plant are also provided. The methods comprise introducing into a plant an expression cassette containing a plant promoter operably linked to a Frk1 and or Frk2 polynucleotide. The Frk1 and or Frk2 may may be linked to the promoter in a sense or an antisense orientation. The expression cassette can be introduced into the plant by any number of means known in the art, including use of *Agrobacterium tumefaciens* vector or through a sexual cross.

Methods of enhancing fructokinase expression in a plant are also provided. The methods comprise introducing into a plant an expression cassette containing a plant promoter operably linked to a Frk1 and or Frk2 polynucleotide. The Frk1 and or Frk2 may encode a Frk1 and or Frk2 polypeptide. The expression cassette can be introduced into the plant by any number of means known in the art, including use of *Agrobacterium tumefaciens* vector or through a sexual cross.

The promoters of the invention can be used in methods of targeting expression of a desired polynucleotide to fruits or other organs of a plant. The methods comprise introducing into a plant an expression cassette containing a tissue-specific, for example, a fruit ripening-specific, promoter operably linked to a Frk1 and or Frk2 polynucleotide sequences.

DEFINITIONS

The term "antisense" refers to sequences of nucleic acids that are complementary to the coding mRNA nucleic acid sequence of a target gene. A DNA sequence linked to a promoter in an "antisense orientation" is linked to the promoter such that an RNA molecule complementary to the coding mRNA of the target gene is produced.

The term "exogenous polynucleotide" refers to a polynucleotide which is introduced into the plant by any means other than by a sexual cross. Examples of means by which this can be accomplished are described below, and include Agrobacterium-mediated transformation, biolistic methods, electroporation, in planta techniques, and the like. Such a plant containing the exogenous nucleic acid is referred to here as an $R_1$ generation transgenic plant. Transgenic plants which arise from sexual cross or by selfing are descendants of such a plant.

The term "isolated nucleic acid molecule" or "isolated protein" refers to a nucleic acid or protein which is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated Frk1 gene is separated from open reading frames which flank the gene and encode a protein other than Frk1. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "operably linked" refers to functional linkage between a promoter and a second sequence, wherein the promoter sequence initiates transcription of RNA corresponding to the second sequence.

The term "plasmid" refers to a circular double stranded DNA molecule which comprises the coding sequence of interest, regulatory elements, a selection marker and optionally an amplification marker. A plasmid can transform prokaryotic cells or transfect eukaryotic cells.

The term "polypeptide" refers to an amino acids connected by peptide bonds. Polypeptides can be entire proteins or portions thereof For example, a Frk1 polypeptide may refer to the entire Frk1 protein or fragments of the Frk1 protein.

The term "polynucleotide," "polynucleotide sequence" or "nucleic acid sequence" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular Frk1 nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene. A "Frk1 polynucleotide" is a nucleic acid sequence comprising (or consisting of) a coding region (exclusive of introns) of about 1500 to about 2000 nucleotides, sometimes from about 1800 to about 1900 nucleotides, which hybridizes to SEQ. ID. No. 1 under stringent conditions (as defined below), or which encodes a Frk1 polypeptide. Frk1 polynucleotides can also be identified by their ability to hybridize under low stringency conditions (e.g., $T_m$–40° C.) to nucleic acid probes having a sequence of 8 to 300 bases, preferably a sequence of 80 to 100 bases in SEQ ID NO: 1.

The term "promoter" refers to a nucleic acid sequence that directs expression of a coding sequence. A promoter can be constitutive, i.e., relatively independent of the stage of differentiation of the cell in which it is contained or it can be inducible, i.e., induced be specific environmental factors, such as the length of the day, the temperature, etc. or a promoter can be tissue-specific, i.e., directing the expression of the coding sequence in cells of a certain tissue type.

The term "sense" refers to sequences of nucleic acids that are in the same orientation as the coding mRNA nucleic acid sequence. A DNA sequence linked to promoter in a "sense orientation" is linked such that an RNA molecule which contains sequences identical to an mRNA is transcribed. The produced RNA molecule, however, need not be transcribed into a functional protein. As used here, an mRNA is an RNA molecule which is translated by ribosomes into polypeptides.

The term "specifically hybridizes" refers to a nucleic acid probe that hybridizes, duplexes or binds to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., MOLECULAR CLONING: A LABORATORY MANUAL (2ND ED.), Vols. 1–3, Cold Spring Harbor Laboratory, (1989) ("Sambrook") or CURRENT PROTOCOLS IN MOLECULAR BIOLOGY, F. Ausubel et al., ed. Greene Publishing and Wiley-Interscience, New York (1987) ("Ausubel").

The term "stringent conditions" in the context of nucleic acid hybridization experiments such as Southern and northern hybridizations refers to sequence dependent, binding and washing environments. An extensive guide to the hybridization of nucleic acids is found in Tijssen (1993) LABO- RATORY TECHNIQUES IN BIOCHEMISTRY AND MOLECULAR BIOLOGY—HYBRIDIZATION WITH NUCLEIC ACID PROBES part I chapter 2 "overview of principles of hybridization and the strategy of nucleic acid probe assays", Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formalin with 1 mg of heparin at between 40 and 50° C., preferably 42° C., with the hybridization being carried out overnight. An example of highly stringent wash conditions is 0.15M NaCl at from 70 to 80° C. with 72° C. being preferable for about 15 minutes. An example of stringent wash conditions is a 0.2× SSC wash at about 60 to 70° C., preferably 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1× SSC at 40 to 50° C., preferably 45° C. for 15 minutes. An example low stringency wash for a duplex of, e.g., more than 100 nucleotides, is 4–6× SSC at 35 to 45° C., with 40° C. being preferable, for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

DETAILED DESCRIPTION OF THE INVENTION

The present invention provides fructokinase nucleic acids referred to here as Frk1. The nucleic acid sequence can be used to modulate expression of endogenous fructokinases in fruit or other organs of a transgenic plant. For instance, the nucleic acids can be used to inhibt expression of an endogenous Frk1 gene, thus providing for sweeter fruit or other organs. In addition, the coding sequences of another fructokinase gene (Frk2), highly homologous to other fructokinase genes, can be used with Frk1 to modify the carbohydrate composition of fruits and organs. As explained below, a number of means can be used to modulate expression of the endogenous genes.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook, et. al., MOLECULAR CLONING—A LABORATORY MANUAL, 2ND. ED., Cold Spring Harbor Laboratory, Cold Spring Harbor, N.Y., (1989).

A. Isolation of Nucleic Acid Sequences from Plants

The isolation of sequences of the invention may be accomplished by a number of techniques. For instance, oligonucleotide probes based on the sequences disclosed here can be used to identify the desired Frk1 gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying fructokinase-specific genes from plant tissues are generated from comparisons of the sequences provided herein. For a general overview of PCR see PCR PROTOCOLS: A GUIDE TO METHODS AND APPLICATIONS, (Innis, M, Gelfand, D., Sninsky, J. and White, T., eds.), Academic Press, San Diego (1990). Appropriate primers for this invention include, for instance: a 5' PCR primer [5'-GGIGGIGCICCIGCIAA(CT)G T-3'] (SEQ ID NO:3) and a 3' PCR primer [5'(AG)TCNCCNGCNCCNGTNGT(AG)TC-3'] (SEQ ID NO:4) where I is inosine and N denotes all nucleotides. To amplify a Frk1 sequence using these primers, the amplifications conditions are typically as follows. Reaction components: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per mL Taq polymerase. Program: 96° C. for 3 min., 30 cycles of 96° C. for 45 sec., 50° C. for 60 sec., 72° C. for 60 sec, followed by 72° C. for 5 min.

Polynucleotides of the invention may also be synthesized by well-known techniques as described in the technical literature. See, e.g., Carruthers, et al., *Cold Spring Harbor Symp. Quant. Biol.* 47:411–418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

B. Use of Nucleic Acids of the Invention to Inhibit Gene Expression

The isolated sequences prepared as described herein, can be used to prepare expression cassettes useful in a number of techniques. For example, expression cassettes of the invention can be used to suppress endogenous Frk1 gene expression. Inhibiting expression can be useful, for instance, in suppressing the conversion of Fru to Fru-6-P, thus accumulating Fru in the fruits and other organs (e.g., stems, leaves, flowers, seeds, roots, tubers, and the like) of plants. Those organs in which Fru accumulates will be sweeter as a result.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy, et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of Frk genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al., *Nature* 334:585–591 (1988).

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli, et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

C. Use of Nucleic Acids of the Invention to Enhance Gene Expression

The polynucleotides of the invention can be used to modulate other aspects of carbohydrate metabolism in plants. For instance, in some embodiments, overexpression of fructokinase may be desirable. Starch biosynthesis in storage tissues, e.g., tubers, roots, seeds and the like, requires the activity of fructokinase to supply substrates for import to plastids where starch is synthesized. In some tissues, fructokinase has been suggested to be rate-governing for substrate delivery to starch biosynthesis. In these cases, the overexpression of fructokinase is useful in promoting starch synthesis. The polynucleotides of the invention are particularly useful because, unlike other characterized fructokinase genes, their gene products are not inhibited by fructose. Thus the kinetic properties of the product of the newly discovered fructokinase gene are useful in a variety of metabolic contexts.

The isolated sequences prepared as described herein can also be used to prepare expression cassettes which enhance or increase Frk1 gene expression. In addition to endogenous Frk1 and Frk2 expression, the exogenous polynucleotides are expressed by the cell.

The exogenous Frk1 and or Frk2 polynucleotides do not have to code for exact copies of the endogenous Frk1 and or Frk2 proteins. Modified Frk1 and or Frk2 protein chains can also be readily designed utilizing various recombinant DNA techniques well known to those skilled in the art and described for instance, in Sambrook et al., supra. Hydroxy-lamine can also be used to introduce single base mutations into the coding region of the gene (Sikorski, et al., *Meth. Enzymol.* 194: 302–318 (1991)). For example, the chains can vary from the naturally occurring sequence at the primary structure level by amino acid substitutions, additions, deletions, and the like. These modifications can be used in a number of combinations to produce the final modified protein chain.

D. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising, et al., *Ann. Rev. Genet.* 22:421–477 (1988). A DNA sequence coding for the desired polypeptide, for example a cDNA sequence encoding the full length Frk1 protein, will preferably be combined with transcriptional and translational initiation regulatory sequences which will direct the transcription of the sequence from the gene in the intended tissues of the transformed plant.

Promoters can be identified by analyzing the 5' sequences of a genomic clone corresponding to the fructokinase-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing, et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855–866 (1989); Bustos, et al., *Plant Cell* 1:839–854 (1989); Green, et al., *EMBO J.* 7:4035–4044 (1988); Meier, et al., *Plant Cell* 3:309–316 (1991); and Zhang, et al., *Plant Physiology* 110:1069–1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. The tissue specific E8 promoter from tomato is particularly useful for directing gene expression so that a desired gene product is located in fruits. The isolation and sequence of the E8 promoter is described in detail in Deikman and Fischer, *EMBO J.* 7:3315–3327 (1988). Other suitable promoters include those from genes encoding embryonic storage proteins. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

E. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et. al., *Embo J.* 3:2717–2722 (1984). Electroporation techniques are described in Fromm, et. al., *Proc. Natl. Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are well described in the scientific literature. See, for example Horsch, et al., *Science* 233:496–498 (1984), and Fraley, et al., *Proc. Nat'l. Acad. Sci. USA* 80:4803 (1983).

Transformed plant cells which are derived by any of the above transformation techniques can be cultured to regenerate a whole plant which possesses the transformed genotype and thus the desired phenotype such as increased sweetness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York, 1983; and Binding, REGENERATION OF PLANTS, PLANT PROTOPLASTS, pp. 21–73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467–486 (1987).

To determine the presence of a reduction or increase of Frk1 activity, an enzymatic assay can be used. One of skill will recognize there are many different types of enzymatic assays that can be used, depending on the substrate used and the method of detecting the increase or decrease of a reaction product or by-product. For example, radiolabeled ATP can be included in the reaction mixture and the increase of radioactive Fru-6-P measured. In one embodiment, crude enzyme extracts from plants are incubated with fructose, ATP, and $NAD^+$. The reduction of NAD+ to NADH+H is monitored continuously at 340 nm. In a preferred enzyme assay, as described in Huber and Kakzawa in *Plant Physiol.* 81:1008 (1985), crude enzyme extracts are incubated with $NAD^+$, ATP, $NAD^+$ dependent Glc-6-P dehydrogenase. For assay of Fru phosphorylation, phosphogluco isomerase is added and the reaction initiated with 2 mM Fru. Reactions are monitored continuously by absorption at 340 nm.

One of skill will recognize that other assays can be used to detect the presence or absence of Frk1. These assays include but are not limited to, immunoassays, electrophoretic detection assays (either with staining or western blotting), and carbohydrate detection assays.

The nucleic acids of the invention can be used to confer desired traits on essentially any plant. Thus, the invention has use over a broad range of plants, including species from the genera Asparagus, Avena, Brassica, Citrus, Citrullus, Capsicum, Cucumis, Cucurbita, Daucus, Fragaria, Glycine, Hordeum, Lactuca, Lycopersicon, Malus, Manihot, Nicotiana, Oryza, Persea, Pisum, Pyrus Prunus, Raphanus, Secale, Solanum, Sorghum, Triticum, Vitis, Vigna, and Zea. The Frk1 genes of the invention are particularly useful in the production of transgenic plants in the genus Lycopersicon.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

EXAMPLES

The following examples are offered to illustrate, but not to limit the claimed invention.

Example 1
PCR Amplification and Sequencing of Tomato Fructokinase cDNA

Amino acid alignment of fructokinase sequences from potato (Smith, et al., (1993) and three bacteria (Aulkemeyer, P., et al., *Mol. Microbiol.* 5:2913 (1991); Blatch, G. L., et. al., *Gene* 95:17 (1990)) were used to identify two conserved domains for the construction of degenerate PCR primers. The conserved domain sequences corresponded to amino acids 43–49 and 252–258 of potato fructokinase. These amino acid sequences were used to design the 5' PCR primer [5'-GGIGGIGCICCIGCIAA(CT)G T-3'] (SEQ ID NO:3) and the 3' PCR primer [5'(AG)TCNCCNGCNCCNGTNGT (AG)TC-3'] (SEQ ID NO:4) where I is inosine and N denotes all nucleotides. PCR was carried out with tomato cDNA library from ripe fruit, according to the method disclosed in DellaPenna, D., et al., *Proc. Nat'l Acad. Sci. USA* 83:6420 (1986). Amplifications were for 40 cycles, each consisting of 1 min at 94° C., 1 min at 45° C., and 1 min at 72° C. Several PCR products derived from ripe fruit cDNA were sequenced and one was identified as Frk1. This fragment was approximately 680 bp DNA fragment and was agarose gel purified and cloned into the pCRII™ (Invitrogen, San Diego, Calif.) plasmid vector according to the manufacturer's instructions. DNA sequencing by the dideoxy chain termination method was performed using the Sequenase®, ver. 2 kit from United States Biochemical according to its instructions.

Example 2
Tomato Frk1 cDNA Isolation and Characterization

A tomato root cDNA library in λZAP H was screened with the Frk1 PCR product described in Example 1 or with potato fructokinase cDNA. Screening probes were prepared by random priming with [α-$^{32}$P]dATP and hybridization was carried out in 50% (v/v) formamide, 6× SSPE (see Sambrook, supra), 5× Denhardt's reagent, 0.5% (w/v) SDS, 100 μg/mL denatured salmon sperm DNA at 42° C. (Frk1) or 37° C. (potato fructokinase. Filters were washed in 0.5× SSC, 0.1% SDS at 58° C. pBluescript containing cDNA insert that only hybridized with the Frk1 PCR product was excised from selected clones and completely sequenced on both strands (SEQ ID NO: 1).

The complete nucleotide sequence of the Frk1 cDNA which contains 1887 bp plus a polyA$^+$ tail is accessible through its GenBank accession number U64817 (SEQ ID NO:1). The cDNA contained an open reading frame that encoded a protein of 347 amino acids with a calculated molecular mass of 37,308 daltons. The ATG triplet beginning at nucleotide position 271 was assigned as the likely site of translation initiation because there was an in-frame termination codon (TGA) at positions 1312–1314, and 6 of 9 nucleotides surrounding the ATG triplet were identical with the proposed consensus sequence of AACA<u>ATG</u>GC for plant initiation codons (Lutcke,H., et al., *EMBO J.* 6:43 (1987)). A putative polyadenylation signal was located 31 bp upstream from the polyadenylation start site.

The deduced amino acid sequence of Frk1 (SEQ ID NO:2) was 28 amino acids longer than the deduced amino acid sequence from potato fructokinase cDNA as demonstrated by Smith, S. B., et al., *Plant Physiol.* 102:1043 (1993). The amino acid sequence identity between Frk1 and potato fructokinase was only 55%, but several domains implicated in fructokinase function were conserved between the Frk1 sequence and other fructokinases. There was no sequence similarity between Frk1 and Arabidopsis hexokinase (Dai, N., et al., *Plant Physiol.* 108:879 (1995)), an enzyme which phosphorylates both Glc and Fru.

The complete Frk2 cDNA nucleotide sequence comprised of 1261 bp plus a polyA$^+$ tail is accessible through its GenBank accession number U64818 (SEQ ID NO:5). The cDNA contained an open reading frame that encoded a predicted protein of 328 amino acids with a calculated molecular mass of 34,761 D (SEQ ID NO:6). The ATG triplet beginning at nucleotide 62 was assigned as the likely site of translation initiation because there was a termination codon (TAG) at positions 1046–1048, and 7 of 9 nucleotides surrounding the ATG triplet were identical with the proposed consensus sequence for plant initiation codons as described above. An AATAAA motif was located at 71 bp upstream from the polyadenylation site and a GT-rich sequence was also located upstream from the motif in the 3'-untranslated region. In plant mRNAs, an AAUAAA-like sequence is typically located 10–30 nucleotides upstream from the polyadenylation site and a GU-rich sequence located upstream from the polyadenylation signal (Wu, L., et al., *Plant J.* 8:323 (1995)). Because there were no other AATAAA-like sequences between the AATAAA motif and the polyadenylation site in the 3' untranslated region of Frk2 cDNA, it is appears that the Frk2 transcript has a polyadenylation signal unusually far from the polyadenylation site. The deduced amino acid sequence of Frk2 (SEQ ID NO: 6) is 93% identical with potato fructokinase but only 57% identical to tomato Frk1.

Example 3
Characterization of Frk1 Gene Product

To provide enough protein for characterization, the Frk1 gene was expressed in yeast. The yeast strain used was DFY632-MATa, ura3-52, hxk1;;LEU2, hxk2;;LEU2, glk1::LEU2, lys1-1, leu2-1 (DFY632). Yeast cells were grown on YEPG media, consisting of 1% Yeast Extract (all of the following reagents were from Difco unless otherwise noted), 2% Bacto Peptone™ and 110 mM galactose (Sherman, et al., METHODS IN YEAST GENETICS: LABORATORY MANUAL, Cold Spring Harbor Laboratory, Cold Spring Harbor, N.Y. (1986)). Selective media for uracil auxotrophic growth, URA+sugar, contained 0.5% ammonium sulfate, 0.17% Yeast Nitrogen Base without amino acids, 0.2% Casamino Acids™, 0.004% adenine (Sigma), 0.008% tryptophan (Sigma) and 110 mM of either Gal, Fru or Glc.

A yeast shuttle vector, pFL61, containing the URA3 gene as a selective marker and the constitutive phosphoglycerate kinase (PGK) promoter and terminator (Minet, M., et al., *Plant J.* 2:417 (1992)) was used for transformation. Frk1 cDNA was cloned downstream of the PGK promoter in pFL61 (pFL61-Frk 1. Yeast transformations were carried out by growing DFY632 cells in YEPG liquid media to mid-logarithmic phase, treating the cells with lithium acetate (Ito, H., et al., *J. Bacteriol.* 153:163 (1983)) and selecting for transformants on −URA+Gal plates.

DFY632 yeast cells transformed with either pFL61 or with pFL61-Frk1 were grown in 40 mL of −URA+Gal liquid media for 72 hours to approximately $5 \times 10^7$ cells/mL. Cells were centrifuged for 5 min at 6000 rpm and washed twice with water and resuspended in 0.5 mL water. 250 μL of the cells were extracted 2 times with 500 μL of Extraction Buffer (50 mM HEPES, pH 7.5, 1 mM EDTA and 1 mM PMSF) by vortexing with 250 μL glass beads. Following vortexing for 3×30 sec, the mixture was centrifuged for 5 min at 12,000 g, 4° C. and the supernatant was brought to 80% ammonium sulfate. After centrifugation at 12,000 g, 4° C., the pellet was resuspended in 0.5 mL Washing Buffer (50 mM HEPES, pH 7.5, 1 mM EDTA and 1 mM DTT), desalted on a G-25 Sephadex® column and used as the crude enzyme extract for subsequent enzymatic analysis.

Hexose kinase activity was measured by an enzyme linked assay according to a modification of Huber and Akazawa in *Plant Physiol* 81:1008 (1985). Assays contained, in a total volume of 1 mL, 30 mM HEPES-NaOH, pH 7.5, 1 mM MgCl$_2$, 0.6 mM EDTA, 9 mM KCl, 1 mM NAD$^+$, 1 mM ATP, 2 U NAD$^+$ dependent Glc-6-P dehydrogenase. For assay of Glc phosphorylation, the reaction was initiated with 2 mM Glc. For assay of Fru phosphorylation, 2 U of phosphogluco isomerase were added and the reaction was initiated with 2 mM Fru. Reactions were carried out at 37° C. and absorption at 340 nm was monitored continuously.

Results

The potato fructokinase cDNA was demonstrated to encode an authentic fructokinase by assay of its in vitro transcription and translation product (Taylor, M. A., et al., *J. Plant Physiol.* 145:253 (1995)). The high sequence similarity between tomato Frk2 and the potato fructokinase cDNA (93% identity) strongly suggests that Frk2 encodes an authentic fructokinase.

To determine whether the Frk1 cDNA also encodes an authentic but divergent fructokinase isozyme, we cloned the Frk1 cDNA into a yeast expression vector pFL61 and expressed the cloned cDNA in DFY 632 triple mutant yeast cells which are unable to phosphorylate either Glc or Fru (Walsh, R. B., et al., *Genetics* 128:521 (1991)). Cells with pFL61 containing Frk1 cDNA (pFL61-Frk1) grew on Fru but not on Glc, indicating that the product of Frk1 cDNA phosphorylates Fru but not Glc. Protein extracts from cells transformed with pFL61-Frk1 phosphorylated Fru but not Glc while protein extracts from cells transformed with pFL61 as a control were unable to phosphorylate either Fru or Glc (Table 1).

TABLE 1

Hexose Kinase Activity in Crude Enzyme Yeast Extracts

| Plasmid | Substrate | Activity (nmole/mg protein min) |
|---|---|---|
| pFL61-Frk1 | Fructose | 127 |
|  | Glucose | 0 |
| pFL61 | Fructose | 0 |
|  | Glucose | 0 |

Example 4
Nucleic Analysis of Tomato Tissues

RNA Analysis

Tissues of tomato (*Lycopersicon esculentum* Mill.) cv T5 were collected from mature plants grown in a greenhouse, frozen in liquid N$_2$ and stored at −80° C. Total RNA was isolated from fruit by the hot borate method (Wan and Wilkins, *Anal. Biochem.* 223:7 (1994)) and from vegetative tissues by the phenol/SDS method (Ausubel, supra). PolyA$^+$ RNA was purified by Oligotex-dT™ (Qiagen) and 1 μg from each sample was subjected to electrophoresis through a 1.2% agarose, 10% (v/v) formaldehyde denaturing gel and transferred to Hybond-N membrane (Amersham). The resulting hybridized with the Frk1 PCR product or the entire insert of Frk2 cDNA as described in Example 2 and washed in 0.5× SSC, 0.1% SDS at astringency of $T_m$−25° C. The blots were exposed to X-ray film (DuPont) with an intensifying screen at −80° C. for 2 days.

DNA Analysis

Genomic DNA was prepared from tomato roots (Murrey and Thompson, *Nucl. Acids Res.* 8:4321 (1980)), and 7.4 μg samples were digested with the restriction endonucleases EcoR1, EcoRV, and Xba1, fractionated on 0.8% agarose gels, and transferred to Hybond-N® membranes. The resulting blot was hybridized with the Frk1 PCR product, a 683 bp of EcoR1 fragment from Frk2 cDNA or the entire insert of potato fructokinase cDNA at 37° C. in the hybridization solution described above, washed in 0.5× SSC, 0.1% SDS at 56° C., and then exposed to X-ray film with an intensifying screen at −80° C. for 1 day.

Results

The 1.9 kb Frk1 mRNA was detected in leaves, stems, roots and fruit and its levels were similar in all three vegetative tissues. Although the 1.2 kb Frk2 mRNA was also detected in all organs examined, the abundance of the Frk2 mRNA was much lower in leaves than in stems and roots. In developing fruit, the level of Frk1 mRNA was low in young green fruit and then increased in immature green fruit and remained at relatively high levels throughout ripening. In contrast, the levels of Frk2 mRNA were very high in young developing fruit but declined to much lower levels in mature green fruit and continued to decline during the early stage of fruit ripening. The highest levels of Frk2 mRNA corresponded to the developmental period of starch accumulation and corresponding high levels of sucrose synthase activity (Robinson, N. L., et al., *Plant Physiol.* 87:727 (1988); Yelle, S., et al., *Plant Physiol.* 87:737 (1988)).

Southern blot analyses was carried out on tomato genomic DNA digested with three restriction enzymes. The Frk1 probe hybridized to a single band in each restriction digests, suggesting the presence of a single gene. The Frk2 cDNA probe hybridized to single restriction fragments that were distinct from those identified by Frk1. The potato fructokinase cDNA hybridized to the same genomic restriction fragments identified by Frk2. The results suggest that, in tomato, there are two distinct fructokinase genes which are sufficiently divergent that they fail to cross-hybridize. Based on hybridization of Southern blots with the potato fructokinase cDNA, Frk2 appears to represent the tomato homologue of this previously characterized potato fructokinase gene.

Example 5

Suppression of Fructokinase Gene Products in Tomato

Gene constructs containing Frk1 and Frk2 nucleic acid coding sequences can be transferred into tomato plants using the Agrobacterium-based gene transfer vectors and selecting transgenic plants with altered fructokinase levels and altered phenotype. The metabolic effect of transgenic suppression of fructokinase expression can be predicted to result in a significant conversion of glucose to fructose in fruit tissue. To avoid negative impact on respiratory pathways, the vectors can be engineered so that the metabolic changes occur in ripening fruit, a developmental period likely to be less sensitive to respiratory perturbation. This can be done by using a ripening-specific promoter. An example of a method to practice the invention is to construct a chimeric gene containing the tomato E8 promoter, a ripening-specific promoter, linked to a part or all of the Frk1 coding sequence and transform tomato plants with this chimeric gene construct. Because the expression of plant genes can be suppressed by expression of either an antisense or sense transgene, the chimeric gene can be constructed to contain the Frk1 coding sequence in either a sense or antisense orientation relative to the E8 promoter sequence. Because there are two distinct and divergent fructokinase genes expressed in tomato fruit, it is may be desirable to suppress the expression of Frk1 and Frk2. This can be accomplished by insertion of tandem gene constructs on a single transformation plasmid or by carrying out separate transformations and combining the transgenes by sexual methods. Selected transgenic plants that have suppressed expression of fructokinase will be used to transfer the trait to commercial varieties by standard genetic crosses. The resulting tomato varieties can be used by fresh market or processing tomato growers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated nucleic acid molecule comprising an Frk1 polynucleotide which remains hybridized to SEQ ID NO:1 during a 0.2× SSC wash at 65° C. for 15 minutes.

2. The isolated nucleic acid molecule of claim 1, wherein the Frk1 polynucleotide is between about 1500 and about 2000 nucleotides in length.

3. The isolated nucleic acid molecule of claim 1, wherein the Frk1 polynucleotide is SEQ ID NO:1.

4. The isolated nucleic acid molecule of claim 1, wherein the Frk1 polynucleotide encodes a Frk1 polypeptide of between about 300 and about 400 amino acids.

5. The isolated nucleic acid molecule of claim 4, wherein the Frk1 polypeptide has an amino acid sequence as shown in SEQ ID NO: 2.

6. The isolated nucleic acid molecule of claim 1, further comprising a plant promoter operably linked to the Frk1 polynucleotide.

7. The isolated nucleic acid molecule of claim 6, wherein the Frk1 polynucleotide is linked to the promoter in the antisense orientation.

8. An isolated nucleic acid molecule comprising a Frk1 polynucleotide, which polynucleotide encodes a Frk1 polypeptide of between about 300 and about 400 amino acids and has an amino acid sequence as shown in SEQ ID NO:2.

9. A method of modifying sweetness in tissues of a transgenic plant, the method comprising introducing into the plant an expression cassette comprising a promoter operably linked to an Frk1 polynucleotide that specifically hybridizes to SEQ ID NO:1 under stringent conditions.

10. The method of claim 9, wherein the Frk1 polynucleotide is linked to the promoter in the antisense orientation.

11. The method of claim 9, wherein the Frk1 polynucleotide is exogenous to the plant.

12. The method of claim 9, wherein the introduction of Frk1 polynucleotide into a plant is by sexual reproduction.

13. The method of claim 9, wherein the promoter is derived from plants.

14. The method of claim 13, wherein the promoter is fruit-specific.

15. The method of claim 14, wherein the promoter is from a tomato E8 gene.

16. The method of claim 9, wherein the promoter is constitutive.

17. A method of promoting starch biosynthesis in the tissues of a transgenic plant, the method comprising introducing into the plant an expression cassette comprising a promoter operably linked to an Frk1 polynucleotide that specifically hybridizes to SEQ ID NO:1 under stringent conditions.

18. The method of claim 17, wherein the Frk1 polynucleotide is exogenous to the plant.

19. The method of claim 17, wherein the introduction of Frk1 polynucleotide into a plant is by sexual reproduction.

20. The method of claim 17, wherein the promoter is derived from plants.

21. The method of claim 17, wherein the promoter is constitutive.

22. A transgenic plant comprising an expression cassette comprising a promoter operably linked to an Frk1 polynucleotide that specifically hybridizes to SEQ ID NO: 1 under stringent conditions.

23. The transgenic plant of claim 22, wherein the Frk1 polynucleotide is operably linked to the promoter in the antisense orientation.

24. The transgenic plant of claim 22, wherein the promoter is derived from plants.

25. The transgenic plant of claim 24, wherein the promoter is fruit specific.

26. The transgenic plant of claim 25, wherein the promoter is from a tomato E8 gene.

27. The transgenic plant of claim 22, wherein the promoter is constitutive.

28. The transgenic plant of claim 22, which is a member of the genus Lycopersicon.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1907 base pairs
      (B) TYPE: nucleic acid
      (C) STRANDEDNESS: single
      (D) TOPOLOGY: linear    (ii) MOLECULE TYPE: cDNA    (ix) FEATURE:
      (A) NAME/KEY: CDS
      (B) LOCATION: 271..1314
      (D) OTHER INFORMATION: /product= "tomato Frk1"

(xi) SEQUENCE DESCRIPTION: SEQ ID NO:1:

```
GGCACGAGAT TGATCCTCAT TCTGCATAAG AAAATTCCGG TACATTTCAT GCCGTGTCGG      60

TGTCAGCAAG GTACACCAAA AGTAGTAAAC AGGGTGGCAA AAAAGAGGAG GATTTAGCAA     120

TTTGTTGATT TTTCCTTCTT TCTTTCTTTC TTGTCAACTT CAAAACCCCA TCGGCTCTCT     180

TTCAAGGTTC CCCTTTCTTT CTCTATTAAC GCCTCTCTCT GAGTTCTTGT TGATATTTCC     240

AAAGACCCCA TTTTTAACAC TGCTCACAAT ATG GCT GGC GAA TCC ATT TCA GGC     294
                                  Met Ala Gly Glu Ser Ile Ser Gly
                                    1               5

AAT TTA AAA GAC CTT TCC TTG AAT AGA AAT GGT GCG GTG TCA AAG AAG      342
Asn Leu Lys Asp Leu Ser Leu Asn Arg Asn Gly Ala Val Ser Lys Lys
    10              15                  20

TCT CAT TTA GTT GTT TGC TTT GGG GAG ATG CTC ATT GAC TTC ATC CCA      390
```

```
Ser His Leu Val Val Cys Phe Gly Glu Met Leu Ile Asp Phe Ile Pro
 25                  30                  35                  40

ACT GTT GCT GGA GTT TCA CTT GCG GAA GCT CCT GCC TTT GAA AAA GCT          438
Thr Val Ala Gly Val Ser Leu Ala Glu Ala Pro Ala Phe Glu Lys Ala
                 45                  50                  55

CCC GGT GGT GCA CCT GCT AAT GTT GCT GTG TGC ATC TCA AAG TTA GGG          486
Pro Gly Gly Ala Pro Ala Asn Val Ala Val Cys Ile Ser Lys Leu Gly
             60                  65                  70

GGT TCA TCT GCT TTT ATT GGA AAG GTT GGT GAC GAT GAG TTC GGC CGT          534
Gly Ser Ser Ala Phe Ile Gly Lys Val Gly Asp Asp Glu Phe Gly Arg
         75                  80                  85

ATG TTG GCT GAC ATT TTG AAG CAA AAC AAT GTT GAC AAT TCC GGC ATG          582
Met Leu Ala Asp Ile Leu Lys Gln Asn Asn Val Asp Asn Ser Gly Met
     90                  95                 100

CGG TTT GAT CAT GAT GCA AGG ACT GCA CTG GCC TTC ATT ACA CTC ACA          630
Arg Phe Asp His Asp Ala Arg Thr Ala Leu Ala Phe Ile Thr Leu Thr
105                 110                 115                 120

GCT GAA GGT GAG CGG GAG TTC GTG TTT TTC CGT AAT CCT AGT GCT GAT          678
Ala Glu Gly Glu Arg Glu Phe Val Phe Phe Arg Asn Pro Ser Ala Asp
                125                 130                 135

ATG CTT CTT CGG GAG TCA GAA CTC GAT GTA GAT CTT ATT AAA AAG GCC          726
Met Leu Leu Arg Glu Ser Glu Leu Asp Val Asp Leu Ile Lys Lys Ala
            140                 145                 150

ACC ATC TTC CAT TAT GGT TCA ATT AGT TTG ATC GAC GAA CCT TGT AGG          774
Thr Ile Phe His Tyr Gly Ser Ile Ser Leu Ile Asp Glu Pro Cys Arg
        155                 160                 165

TCA ACA CAC CTT GCT GCA ATG GAC ATT GCC AAA AGA TCA GGT AGC ATA          822
Ser Thr His Leu Ala Ala Met Asp Ile Ala Lys Arg Ser Gly Ser Ile
    170                 175                 180

CTG TCG TAT GAT CCA AAC CTG AGA TTG CCT TTA TGG CCT TCA GAA GAT          870
Leu Ser Tyr Asp Pro Asn Leu Arg Leu Pro Leu Trp Pro Ser Glu Asp
185                 190                 195                 200

GCT GCT CGA AGT GGA ATA ATG AGT GTA TGG AAC CTA GCA GAT ATT ATT          918
Ala Ala Arg Ser Gly Ile Met Ser Val Trp Asn Leu Ala Asp Ile Ile
                205                 210                 215

AAG ATA AGT GAG GAT GAA ATT TCA TTC TTG ACT GGA GCC GAC GAT CCA          966
Lys Ile Ser Glu Asp Glu Ile Ser Phe Leu Thr Gly Ala Asp Asp Pro
            220                 225                 230

AAT GAT GAC GAG GTG GTG TTG AAG AGG CTT TTC CAT CCT AAT CTG AAG         1014
Asn Asp Asp Glu Val Val Leu Lys Arg Leu Phe His Pro Asn Leu Lys
        235                 240                 245

CTT TTG CTT GTA ACT GAA GGT TCA GCT GGT TGC AGA TAT TAC ACC AAG         1062
Leu Leu Leu Val Thr Glu Gly Ser Ala Gly Cys Arg Tyr Tyr Thr Lys
    250                 255                 260

GAA TTC AAG GGA AGA GTA AAT TCG ATC AAG GTA AAA GCT GTT GAT ACA         1110
Glu Phe Lys Gly Arg Val Asn Ser Ile Lys Val Lys Ala Val Asp Thr
265                 270                 275                 280

ACT GGT GCT GGT GAT GCA TTT ACT GGT GGA GTT CTC AAG TGT CTA GCT         1158
Thr Gly Ala Gly Asp Ala Phe Thr Gly Gly Val Leu Lys Cys Leu Ala
                285                 290                 295

TCT GAT GCT AGT CTT TAT CAG GAT GAA AAG CGG TTA AGG GAG GCT ATC         1206
Ser Asp Ala Ser Leu Tyr Gln Asp Glu Lys Arg Leu Arg Glu Ala Ile
            300                 305                 310

TTT TTT GCC AAT GTT TGT GCT GCC CTG ACA GTG ACA GGA AGA GGT GGA         1254
Phe Phe Ala Asn Val Cys Ala Ala Leu Thr Val Thr Gly Arg Gly Gly
        315                 320                 325

ATC CCT TCC CTT CCT ACA CAA GAT GCA GTT CGA CAA ACT CTT GCC GAG         1302
Ile Pro Ser Leu Pro Thr Gln Asp Ala Val Arg Gln Thr Leu Ala Glu
    330                 335                 340
```

```
GTC ACT GCA TGAGAAGGCA GAACAAAGTT TTGTTCTCTT CACACTGTAT      1351
Val Thr Ala
345

CTGCATTATT CTAGATTTAT TTTCACAATG ATCGATTTAT TTTGTTTTCG TCTCTGGCAT      1411

CTGTTGGTCG GTTCCTCTCT TTGGAAAGAA GTTGCAGCCA ACGAGACATG CAGGGAAAAA      1471

TAGGGTAGCG CGTCTTCTGT CAGTCATGCA AGGAAATGCT GGAAAGCCTT TTTCGCTAAG      1531

TCAAAATACA AGCTGTTATG TCTCCGTTAC ATATCTGATC CTTGTTACGG ATCCATCAGA      1591

AGCCAAGATA GTGAAGGTTG TTAACATTGG TTATTGAGAT TTACTGCGTG TAGAGAGAAG      1651

AACAAAAGGT GGACATGCAT TTAACGACTA TCAGCTTTTG TTTGTTTTAA TATGTTTCCT      1711

TTTCAAGAAC CTTTCTGTTT TTGTTTCCTT TAAAGTGTCT GTATTATAAG GTGACTTCAA      1771

TGCTGTCTTG ATTAGAAATC AGCAGAACAA AAAATATTAC TTATGCAGTT ATGTGGTTTG      1831

ATGTACTACT CAGAAATCAG AATAATATGA GTCTCATACT GTTGATCTCT TCCATCAAAA      1891

AAAAAAAAAA AAAAA      1907

(2) INFORMATION FOR SEQ ID NO:2:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Gly Glu Ser Ile Ser Gly Asn Leu Lys Asp Leu Ser Leu Asn
 1               5                  10                  15

Arg Asn Gly Ala Val Ser Lys Lys Ser His Leu Val Val Cys Phe Gly
                20                  25                  30

Glu Met Leu Ile Asp Phe Ile Pro Thr Val Ala Gly Val Ser Leu Ala
            35                  40                  45

Glu Ala Pro Ala Phe Glu Lys Ala Pro Gly Gly Ala Pro Ala Asn Val
        50                  55                  60

Ala Val Cys Ile Ser Lys Leu Gly Gly Ser Ser Ala Phe Ile Gly Lys
65                  70                  75                  80

Val Gly Asp Asp Glu Phe Gly Arg Met Leu Ala Asp Ile Leu Lys Gln
                85                  90                  95

Asn Asn Val Asp Asn Ser Gly Met Arg Phe Asp His Asp Ala Arg Thr
            100                 105                 110

Ala Leu Ala Phe Ile Thr Leu Thr Ala Glu Gly Glu Arg Glu Phe Val
        115                 120                 125

Phe Phe Arg Asn Pro Ser Ala Asp Met Leu Leu Arg Glu Ser Glu Leu
    130                 135                 140

Asp Val Asp Leu Ile Lys Lys Ala Thr Ile Phe His Tyr Gly Ser Ile
145                 150                 155                 160

Ser Leu Ile Asp Glu Pro Cys Arg Ser Thr His Leu Ala Ala Met Asp
                165                 170                 175

Ile Ala Lys Arg Ser Gly Ser Ile Leu Ser Tyr Asp Pro Asn Leu Arg
            180                 185                 190

Leu Pro Leu Trp Pro Ser Glu Asp Ala Ala Arg Ser Gly Ile Met Ser
        195                 200                 205

Val Trp Asn Leu Ala Asp Ile Ile Lys Ile Ser Glu Asp Glu Ile Ser
    210                 215                 220

Phe Leu Thr Gly Ala Asp Asp Pro Asn Asp Asp Glu Val Val Leu Lys
```

```
225                 230                 235                 240
Arg Leu Phe His Pro Asn Leu Lys Leu Leu Val Thr Glu Gly Ser
                245                 250                 255
Ala Gly Cys Arg Tyr Tyr Thr Lys Glu Phe Lys Gly Arg Val Asn Ser
                260                 265                 270
Ile Lys Val Lys Ala Val Asp Thr Thr Gly Ala Gly Asp Ala Phe Thr
            275                 280                 285
Gly Gly Val Leu Lys Cys Leu Ala Ser Asp Ala Ser Leu Tyr Gln Asp
    290                 295                 300
Glu Lys Arg Leu Arg Glu Ala Ile Phe Phe Ala Asn Val Cys Ala Ala
305                 310                 315                 320
Leu Thr Val Thr Gly Arg Gly Gly Ile Pro Ser Leu Pro Thr Gln Asp
                325                 330                 335
Ala Val Arg Gln Thr Leu Ala Glu Val Thr Ala
                340                 345

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:3:

GGNGGNGCNC CNGCNAAYGT                                             20

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

RTCNCCNGCN CCNGTNGTRT C                                           21
```

-continued (2) INFORMATION FOR SEQ ID NO:5:

(i) SEQUENCE CHARACTERISTICS:
        (A) LENGTH: 1279 base pairs
        (B) TYPE: nucleic acid
        (C) STRANDEDNESS: single
        (D) TOPOLOGY: linear     (ii) MOLECULE TYPE: cDNA     (ix) FEATURE:
        (A) NAME/KEY: CDS
        (B) LOCATION: 62..1048
        (D) OTHER INFORMATION: /product= "tomato Frk2"

(xi) SEQUENCE DESCRIPTION: SEQ ID NO:5:

```
GGCACGAGAA AATCTATAGA TACACCTATA GATACATATA TTTTCTCTAT TCATCGTAGC        60

C ATG GCA GTT AAC GGT GCT TCT TCT TCT GGT TTG ATC GTC AGT TTC          106
  Met Ala Val Asn Gly Ala Ser Ser Ser Gly Leu Ile Val Ser Phe
  1               5                   10                  15

GGT GAG ATG TTG ATC GAT TTC GTT CCG ACA GTC TCC GGC GTA TCC CTT        154
Gly Glu Met Leu Ile Asp Phe Val Pro Thr Val Ser Gly Val Ser Leu
            20                  25                  30

GCC GAG GCT CCC GGA TTT TTG AAA GCT CCC GGC GGT GCA CCG GCG AAC        202
Ala Glu Ala Pro Gly Phe Leu Lys Ala Pro Gly Gly Ala Pro Ala Asn
        35                  40                  45

GTC GCT ATC GCG GTG ACG AGG CTC GGA GGG AAG TCG GCG TTC GTC GGG        250
Val Ala Ile Ala Val Thr Arg Leu Gly Gly Lys Ser Ala Phe Val Gly
    50                  55                  60

AAA CTC GGC GAC GAT GAG TTC GGT CAC ATG CTC GCC GGG ATT CTG AAA        298
Lys Leu Gly Asp Asp Glu Phe Gly His Met Leu Ala Gly Ile Leu Lys
65                  70                  75

ACG AAC GGC GTA CAA GCC GAA GGA ATT AAT TTT GAC AAG GGC GCC AGG        346
Thr Asn Gly Val Gln Ala Glu Gly Ile Asn Phe Asp Lys Gly Ala Arg
80                  85                  90                  95

ACG GCT TTG GCG TTC GTG ACG CTA CGC GCC GAC GGA GAG CGT GAG TTT        394
Thr Ala Leu Ala Phe Val Thr Leu Arg Ala Asp Gly Glu Arg Glu Phe
                100                 105                 110

ATG TTT TAC AGA AAT CCC AGT GCC GAT ATG TTG CTC ACG CCC GCT GAG        442
Met Phe Tyr Arg Asn Pro Ser Ala Asp Met Leu Leu Thr Pro Ala Glu
            115                 120                 125

TTG AAT CTT GAT CTT ATT AGA TCT GCT AAG GTG TTC CAC TAT GGA TCA        490
Leu Asn Leu Asp Leu Ile Arg Ser Ala Lys Val Phe His Tyr Gly Ser
        130                 135                 140

ATT AGT TTG ATC GTG GAG CCA TGT AGA GCA GCA CAT ATG AAG GCA ATG        538
Ile Ser Leu Ile Val Glu Pro Cys Arg Ala Ala His Met Lys Ala Met
    145                 150                 155

GAA GTA GCA AAG GAG GCA GGG GCA TTG CTC TCT TAT GAC CCA AAC CTT        586
Glu Val Ala Lys Glu Ala Gly Ala Leu Leu Ser Tyr Asp Pro Asn Leu
160                 165                 170                 175

CGT TTG CCG TTG TGG CCT TCA GCA GAA GAG GCC AAG AAG CAA ATC AAG        634
Arg Leu Pro Leu Trp Pro Ser Ala Glu Glu Ala Lys Lys Gln Ile Lys
                180                 185                 190

AGC ATA TGG GAC TCT GCT GAT GTG ATC AAG GTC AGC GAT GTG GAG CTC        682
Ser Ile Trp Asp Ser Ala Asp Val Ile Lys Val Ser Asp Val Glu Leu
            195                 200                 205

GAA TTC CTC ACT GGA AGC AAC AAG ATT GAT GAT GAA TCC GCC ATG TCC        730
Glu Phe Leu Thr Gly Ser Asn Lys Ile Asp Asp Glu Ser Ala Met Ser
        210                 215                 220

TTG TGG CAT CCT AAC TTG AAG CTA CTC TTG GTC ACT CTT GGT GAA AAG        778
Leu Trp His Pro Asn Leu Lys Leu Leu Leu Val Thr Leu Gly Glu Lys
    225                 230                 235
```

```
GGT TGC AAT TAC TAC ACC AAG AAA TTC CAT GGA ACC GTT GGA GGA TTC          826
Gly Cys Asn Tyr Tyr Thr Lys Lys Phe His Gly Thr Val Gly Gly Phe
240                 245                 250                 255

CAT GTG AAG ACT GTT GAC ACC ACT GGA GCT GGT GAT TCT TTT GTT GGT          874
His Val Lys Thr Val Asp Thr Thr Gly Ala Gly Asp Ser Phe Val Gly
                260                 265                 270

GCC CTT CTA ACC AAG ATT GTT GAT GAT CAA ACC ATT CTC GAG GAT GAA          922
Ala Leu Leu Thr Lys Ile Val Asp Asp Gln Thr Ile Leu Glu Asp Glu
            275                 280                 285

GCA AGG TTG AAG GAA GTA CTT AGG TTT TCA TGT GCA TGT GGA GCC ATC          970
Ala Arg Leu Lys Glu Val Leu Arg Phe Ser Cys Ala Cys Gly Ala Ile
        290                 295                 300

ACT ACA ACC AAG AAA GGA GCA ATC CCA GCT TTG CCT ACT GCA TCT GAA         1018
Thr Thr Thr Lys Lys Gly Ala Ile Pro Ala Leu Pro Thr Ala Ser Glu
    305                 310                 315

GCC CTC ACT TTG CTC AAG GGA GGA GCA TAGAAACATC GTGTTATCTT               1065
Ala Leu Thr Leu Leu Lys Gly Gly Ala
320                 325

TTTTCTTTTT TCCATCTTCA TATATTTCCC CCCCTTTATG AGTTTTTTTG AAGCTAGTAG       1125

GAAGCCTTTT CAGTTTTGGA TTTTAATGTT TTGTTGTGAT GAATGTCCAT CAAGACACTT       1185

AATAAACTAA GCTTTCTTCA TATGCAGCTT CCTTGTAACT TCTCCTTTAC ATCATCATAC       1245

TAGTATTTCA TTATCCAAAA AAAAAAAAAA AAAA                                   1279

(2) INFORMATION FOR SEQ ID NO:6:

(i) SEQUENCE CHARACTERISTICS:
        (A) LENGTH: 328 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Val Asn Gly Ala Ser Ser Gly Leu Ile Val Ser Phe Gly
  1               5                  10                  15

Glu Met Leu Ile Asp Phe Val Pro Thr Val Ser Gly Val Ser Leu Ala
                 20                  25                  30

Glu Ala Pro Gly Phe Leu Lys Ala Pro Gly Gly Ala Pro Ala Asn Val
             35                  40                  45

Ala Ile Ala Val Thr Arg Leu Gly Gly Lys Ser Ala Phe Val Gly Lys
         50                  55                  60

Leu Gly Asp Asp Glu Phe Gly His Met Leu Ala Gly Ile Leu Lys Thr
 65                  70                  75                  80

Asn Gly Val Gln Ala Glu Gly Ile Asn Phe Asp Lys Gly Ala Arg Thr
                 85                  90                  95

Ala Leu Ala Phe Val Thr Leu Arg Ala Asp Gly Glu Arg Glu Phe Met
                100                 105                 110

Phe Tyr Arg Asn Pro Ser Ala Asp Met Leu Leu Thr Pro Ala Glu Leu
            115                 120                 125

Asn Leu Asp Leu Ile Arg Ser Ala Lys Val Phe His Tyr Gly Ser Ile
        130                 135                 140

Ser Leu Ile Val Glu Pro Cys Arg Ala Ala His Met Lys Ala Met Glu
145                 150                 155                 160

Val Ala Lys Glu Ala Gly Ala Leu Leu Ser Tyr Asp Pro Asn Leu Arg
                165                 170                 175

Leu Pro Leu Trp Pro Ser Ala Glu Glu Ala Lys Lys Gln Ile Lys Ser
            180                 185                 190
```

```
-continued

Ile Trp Asp Ser Ala Asp Val Ile Lys Val Ser Asp Val Glu Leu Glu
        195                 200                 205

Phe Leu Thr Gly Ser Asn Lys Ile Asp Asp Glu Ser Ala Met Ser Leu
        210                 215                 220

Trp His Pro Asn Leu Lys Leu Leu Val Thr Leu Gly Glu Lys Gly
225                 230                 235                 240

Cys Asn Tyr Tyr Thr Lys Lys Phe His Gly Thr Val Gly Gly Phe His
                245                 250                 255

Val Lys Thr Val Asp Thr Thr Gly Ala Gly Asp Ser Phe Val Gly Ala
                260                 265                 270

Leu Leu Thr Lys Ile Val Asp Asp Gln Thr Ile Leu Glu Asp Glu Ala
        275                 280                 285

Arg Leu Lys Glu Val Leu Arg Phe Ser Cys Ala Cys Gly Ala Ile Thr
    290                 295                 300

Thr Thr Lys Lys Gly Ala Ile Pro Ala Leu Pro Thr Ala Ser Glu Ala
305                 310                 315                 320

Leu Thr Leu Leu Lys Gly Gly Ala
                325
```